(12) United States Patent
Ferek-Petric (10) Patent No.: US 6,650,941 B2
(45) Date of Patent: Nov. 18, 2003

(54) IMPLANTABLE MEDICAL DEVICE PROGRAMMING WANDS HAVING INTEGRAL INPUT DEVICE (75) Inventor: Bozidar Ferek-Petric, Zagreb (HR)

(73) Assignee: Medtronic, Inc., Minneapolis, MO (US)

( * ) Notice: Subject to any disclaimer, the term of this patent is extended or adjusted under 35 U.S.C. 154(b) by 191 days.

(21) Appl. No.: 09/742,118

(22) Filed: Dec. 22, 2000

(65) Prior Publication Data

US 2002/0116032 A1 Aug. 22, 2002

(51) Int. Cl.⁷ .................................................. A61N 1/08
(52) U.S. Cl. ............................. 607/30; 607/32; 607/60
(58) Field of Search .............................. 607/4, 5, 7, 9, 607/30, 32, 60; 128/903, 904

(56) References Cited

U.S. PATENT DOCUMENTS

| 4,316,472 A | 2/1982 | Mirowski et al. ............... 607/9 |
| 4,375,817 A | 3/1983 | Engle et al. ..................... 607/4 |
| 4,379,459 A | 4/1983 | Stein .............................. 607/9 |
| 4,384,585 A | 5/1983 | Zipes .............................. 607/5 |
| 4,476,868 A | 10/1984 | Thompson ..................... 607/14 |
| 4,556,063 A | 12/1985 | Thompson et al. ............ 607/32 |
| 4,577,633 A | 3/1986 | Berkovits et al. ............. 607/15 |
| 4,587,970 A | 5/1986 | Holley et al. .................. 607/15 |
| 4,726,380 A | 2/1988 | Vollmann et al. ............. 607/15 |
| 4,727,877 A | 3/1988 | Kallok ........................... 607/5 |
| 4,800,883 A | 1/1989 | Winstrom ....................... 607/7 |
| 4,821,723 A | 4/1989 | Baker, Jr. et al. ............... 607/7 |
| 4,830,006 A | 5/1989 | Haluska et al. ................. 607/4 |
| 4,880,005 A | 11/1989 | Pless et al. .................... 607/15 |
| 4,949,719 A | 8/1990 | Pless et al. ..................... 607/7 |
| 4,953,551 A | 9/1990 | Mehra et al. ................... 607/5 |
| 5,099,838 A | 3/1992 | Bardy ............................. 607/2 |
| 5,117,824 A | 6/1992 | Keimel et al. .................. 607/4 |
| 5,131,388 A | 7/1992 | Pless et al. ..................... 607/5 |
| 5,144,949 A | 9/1992 | Olson ........................... 607/17 |
| 5,158,078 A | 10/1992 | Bennett et al. ................ 607/27 |
| 5,163,427 A | 11/1992 | Keimel ........................... 607/5 |

(List continued on next page.)

FOREIGN PATENT DOCUMENTS

WO    WO92/18198    10/1992

OTHER PUBLICATIONS

Arzbaecher et al., "Automatic Tachycardia Recognition", *PACE*, 541–547 (May–Jun. 1984).
Olson et al., "IEEE Computer Society Press", *Computers in Cardiology*, 167–170 (Oct. 7–10, 1986).

Primary Examiner—Willis R. Wolfe
(74) Attorney, Agent, or Firm—Thomas E. Woods; Eric R. Waldkoetter; Tom G. Berry (57) ABSTRACT Programming wands, systems and methods are provided for programming implantable medical devices (IMDs). The programming wands of the present invention preferably include one or more input devices which may be manipulated to control the programming process. In some embodiments, the input device includes one or more of a trackball, a button, and a scrolling wheel. By providing input devices on the programming wand, a physician or medical technician may control the programming process with the same hand that supports the programming wand.

7 Claims, 7 Drawing Sheets

U.S. PATENT DOCUMENTS

| | | |
|---|---|---|
| 5,188,105 A | 2/1993 | Keimel .......................... 607/5 |
| 5,199,428 A | 4/1993 | Obel et al. ..................... 607/44 |
| 5,204,768 A | 4/1993 | Tsakiris et al. ........ 340/825.72 |
| 5,207,218 A | 5/1993 | Carpentier et al. ........... 607/36 |
| 5,269,298 A | 12/1993 | Adams .......................... 607/5 |
| 5,312,453 A | 5/1994 | Shelton et al. ................ 607/19 |
| 5,314,430 A | 5/1994 | Bardy .......................... 607/5 |
| 5,330,507 A | 7/1994 | Schwartz ..................... 607/14 |
| 5,331,966 A | 7/1994 | Bennett et al. ............. 600/508 |
| 5,354,316 A | 10/1994 | Keimel ........................ 607/15 |
| 5,354,319 A | 10/1994 | Wyborny et al. .............. 607/32 |
| 5,545,186 A | 8/1996 | Olson et al. ................... 607/14 |
| 5,690,686 A | 11/1997 | Min et al. ....................... 607/5 |
| 5,720,771 A | 2/1998 | Snell ........................... 607/60 |
| 5,759,199 A | 6/1998 | Snell et al. ................... 607/60 |
| 5,785,660 A | 7/1998 | van Lake et al. .............. 607/30 |
| 5,800,465 A | 9/1998 | Thompson et al. ............. 607/9 |
| 5,861,019 A * | 1/1999 | Sun et al. ..................... 607/60 |
| 5,954,666 A | 9/1999 | Snell .......................... 607/32 |
| 6,442,430 B1 * | 8/2002 | Ferek-Petric ................. 607/32 |

* cited by examiner

IMPLANTABLE MEDICAL DEVICE PROGRAMMING WANDS HAVING INTEGRAL INPUT DEVICE

FIELD OF THE INVENTION

The present invention relates to implantable medical devices such as cardiac pacemakers and defibrillators. More particularly, the present invention pertains to implantable medical device programming wands having one or more input devices located thereon and methods for their use.

BACKGROUND

A wide variety of implantable medical devices (IMDs) are known and commercially available. Generally, these devices utilize a bio-compatible case having a connector block mounted thereto. The connector block includes receptacles for leads that may be used for electrical stimulation and/or for sensing physiological activity. For example, an implantable cardiac device, e.g., an implantable pacemaker-cardioverter-defibrillator (PCD), may use such leads to monitor activity of a human heart and to deliver therapy thereto in the event undesirable heart activity is detected.

IMDs typically require programming by an operator, e.g., physician or medical technician, to ensure that the therapy delivered by the IMD corresponds to the specific treatment required by the patient. In modern IMDs, programming is typically accomplished via an external programming apparatus that consists of an integrated computer system incorporating the IMD programming electronics and appropriate programming software, an input device such as a keyboard or digitizing pen for data entry, and an output device, e.g., video monitor, for viewing relevant information regarding the programming process. During operation, a telemetry apparatus, e.g., a programming wand, tethered to the computer system is held near the patient in close proximity to the implanted medical device. Using wireless communication protocols, e.g., bi-directional RF, the telemetry module permits communication between the programming apparatus and the IMD. The operator monitors information pertaining to the programming process on the video monitor and controls various programming functions via the input device.

While effective, these programming apparatus have drawbacks. For example, because space proximate the patient is limited in crowded medical environments, the programming apparatus, including the input device, may not always be conveniently located adjacent to the patient but may rather be located peripherally thereto. In these instances, the operator is required to hold the programming wand near the patient with one hand while reaching to manipulate the input device/programming apparatus with the other. Not only is this technique inconvenient, it may also result in premature operator fatigue. Furthermore, the operator may undesirably need to remove his or her distal hand from the input device to accommodate movement of medical personnel and equipment around the patient.

Exemplary input devices for IMD programmers are mentioned or described in U.S. Pat. No. 5,720,771 to Snell, U.S. Pat. No. 5,759,199 to Snell et al., U.S. Pat. No. 5,785,660 to van Lake et al. and U.S. Pat. No. 5,954,666 to Snell. These documents disclose programmers that utilize input devices which may, for example, be a "touch screen, keyboard, light pen, mouse, trackball or a pen and a digitizing screen" (see U.S. Pat. No. 5,720,771, column 4, lines 15–20).

In addition to the input devices disclosed in the above-identified patent documents, U.S. Pat. No. 5,204,768 to Tsakiris et al., discloses a wireless remote which may be used to control an electronic presentation system.

Accordingly, input devices other than keyboards and digitizing pens are known. However, the systems disclosed in the above-identified documents (which are also listed in Table 1 below) do not address the IMD-programming-specific problems discussed above, e.g., inconvenient two-handed operation in crowded environments.

TABLE 1

| Pat. No.  | Inventor         | Issue Date    |
|-----------|------------------|---------------|
| 5,785,660 | van Lake et al.  | Jul. 28, 1998 |
| 5,759,199 | Snell et al.     | Jun. 2, 1998  |
| 5,720,771 | Snell            | Feb. 24, 1998 |
| 5,954,666 | Snell            | Sep. 21, 1999 |
| 5,204,768 | Tsakiris et al.  | Apr. 20, 1993 |

All documents listed in Table 1 above are hereby incorporated by reference herein in their respective entireties. As those of ordinary skill in the art will appreciate readily upon reading the Summary of the Invention, Detailed Description of the Embodiments, and claims set forth below, many of the devices and methods disclosed in the documents of Table 1 and others documents incorporated by reference herein may be modified advantageously by using the teachings of the present invention

SUMMARY OF THE INVENTION

The present invention has certain objects. That is, various embodiments of the present invention provide solutions to one or more problems existing in the art with respect to IMD programming apparatus. In particular, the present invention addresses problems relating to current programming apparatus and techniques used to program IMDs. One such problem involves fatigue experienced when the operator is required to hold a programming wand with one hand while operating an input device with the other. Other problems include the need to operate the programming apparatus when the input device is not immediately adjacent to the operator.

In comparison to known techniques for programming IMDs, various embodiments of the present invention may provide certain advantages. For instance, execution of the IMD programming process may be controlled via one or more input devices located on the programming wand so that the operator may control the programming process with the same hand that supports the programming wand. As a result, the operator is not required to manipulate the input device/programmer with a second hand while holding the programming wand with the other.

Embodiments of the present invention may provide one or more of the following features. For instance, the invention may provide a programming wand for programming an implantable medical device where the wand may include a housing and an antenna associated with the housing. The antenna may be coupled to transmitter circuitry such that the antenna is able to transmit programming information from a programming device to the implantable medical device. The wand may also include at least one input device coupled to the housing where the input device permits control of the programming device. The input devices may include one or more of a trackball, a button, and a scrolling wheel. In other embodiments, the wand may further include receiver circuitry operable to receive information from the implantable medical device.

Other embodiments of the present invention may provide a method for programming an implantable medical device, where the method comprises one or more of the following features: providing a programming apparatus operable for use in programming an implantable medical device, the apparatus comprising a programming wand; positioning the programming wand proximate to the implantable medical device; transmitting programming instructions from the programming device to the implantable medical device via the programming wand; and manipulating one or more input devices located on the programming wand to control the programming apparatus. The method may further include transmitting device status information from the implantable medical device to the programming wand and transmitting patient status information from the implantable medical device to the programming wand. Manipulation of the input devices may be responsive to one or more of the programming instructions, the device status information, and the patient status information. Manipulation of the input devices may include: rotation of a trackball; rotating a scrolling wheel; and/or depressing a button.

The above summary of the invention is not intended to describe each embodiment or every implementation of the present invention. Rather, a more complete understanding of the invention will become apparent and appreciated by reference to the following detailed description and claims in view of the accompanying drawings.

BRIEF DESCRIPTION OF THE DRAWINGS

The present invention will be further described with reference to the drawings, wherein.

DETAILED DESCRIPTION OF THE EMBODIMENTS

Figure 1:
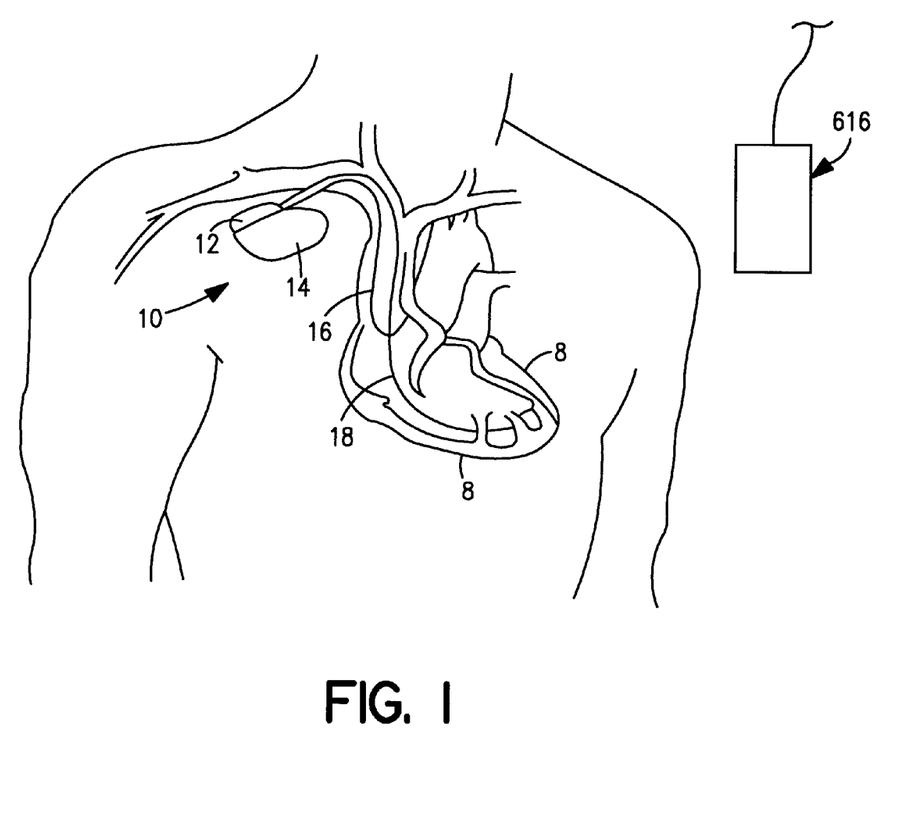
FIG. 1 is an implantable medical device (IMD) and programming wand in accordance with one embodiment of the invention, wherein the IMD is shown implanted within the body of a patient.

FIG. 1 is a simplified schematic view of one embodiment of implantable medical device ("IMD") 10 programmable by a programming system having a programming wand 616 in accordance with the present invention. IMD 10 shown in FIG. 1 is a pacemaker comprising at least one of pacing and sensing leads 16 and 18 attached to hermetically sealed enclosure 14 and implanted near human or mammalian heart 8. Pacing and sensing leads 16 and 18, sense electrical signals attendant to the depolarization and re-polarization of the heart 8, and further provide pacing pulses for causing depolarization of cardiac tissue in the vicinity of the distal ends thereof. Leads 16 and 18 may have, for example, unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al. or U.S. Pat. No. 5,144,949 to Olson.

Figure 2:
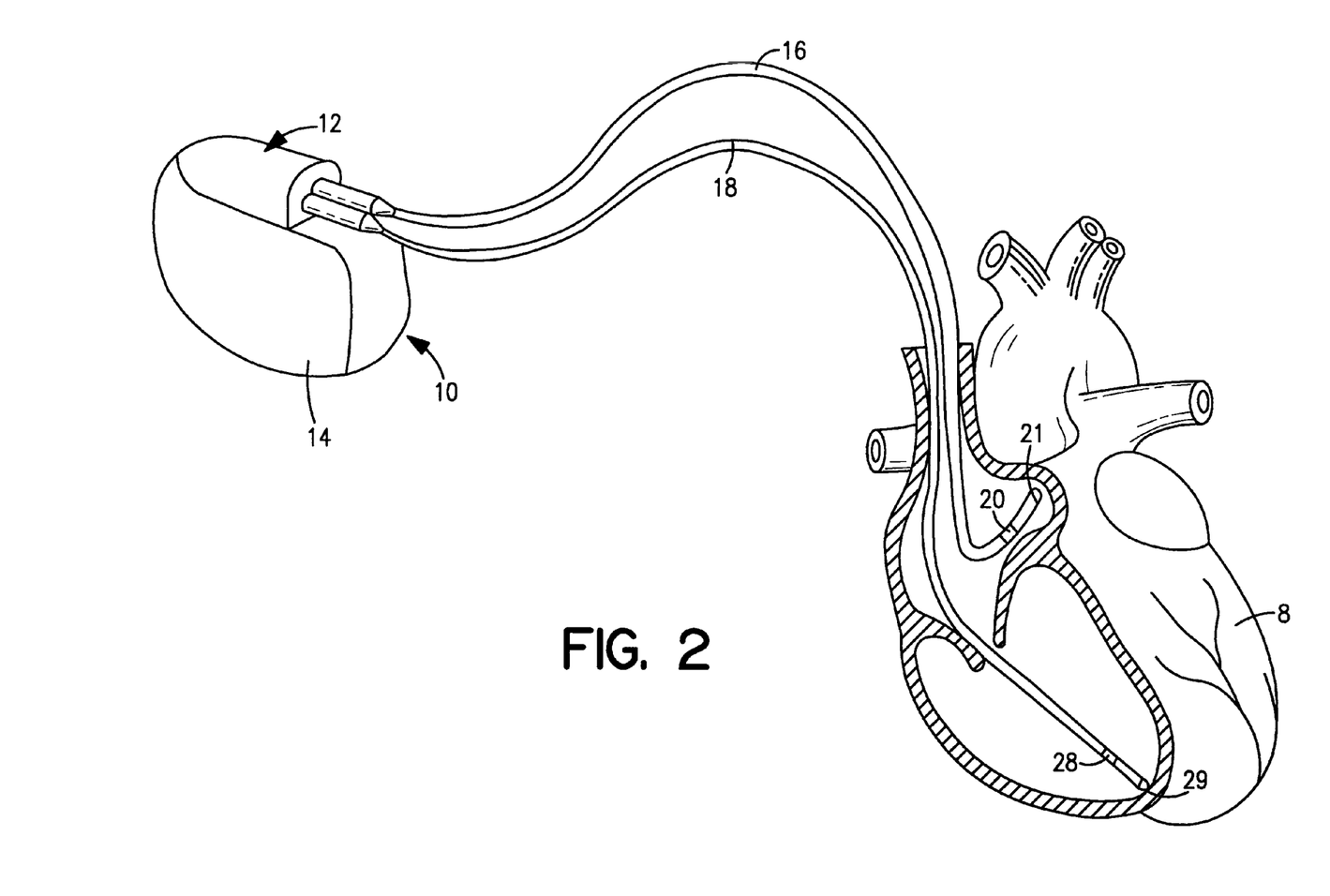
FIG. 2 is an enlarged view of the IMO of FIG. 1 diagrammatically illustrating coupling with the patient's heart in accordance with one embodiment of the invention.

FIG. 2 shows connector module 12 and hermetically sealed enclosure 14 of IMD 10 located near human or mammalian heart 8. Atrial and ventricular pacing leads 16 and 18 extend from connector header module 12 to the right atrium and ventricle, respectively, of heart 8. Atrial electrodes 20 and 21 disposed at the distal end of atrial pacing lead 16 are located in the right atrium. Ventricular electrodes 28 and 29 at the distal end of ventricular pacing lead 18 are located in the right ventricle.

Figure 3:
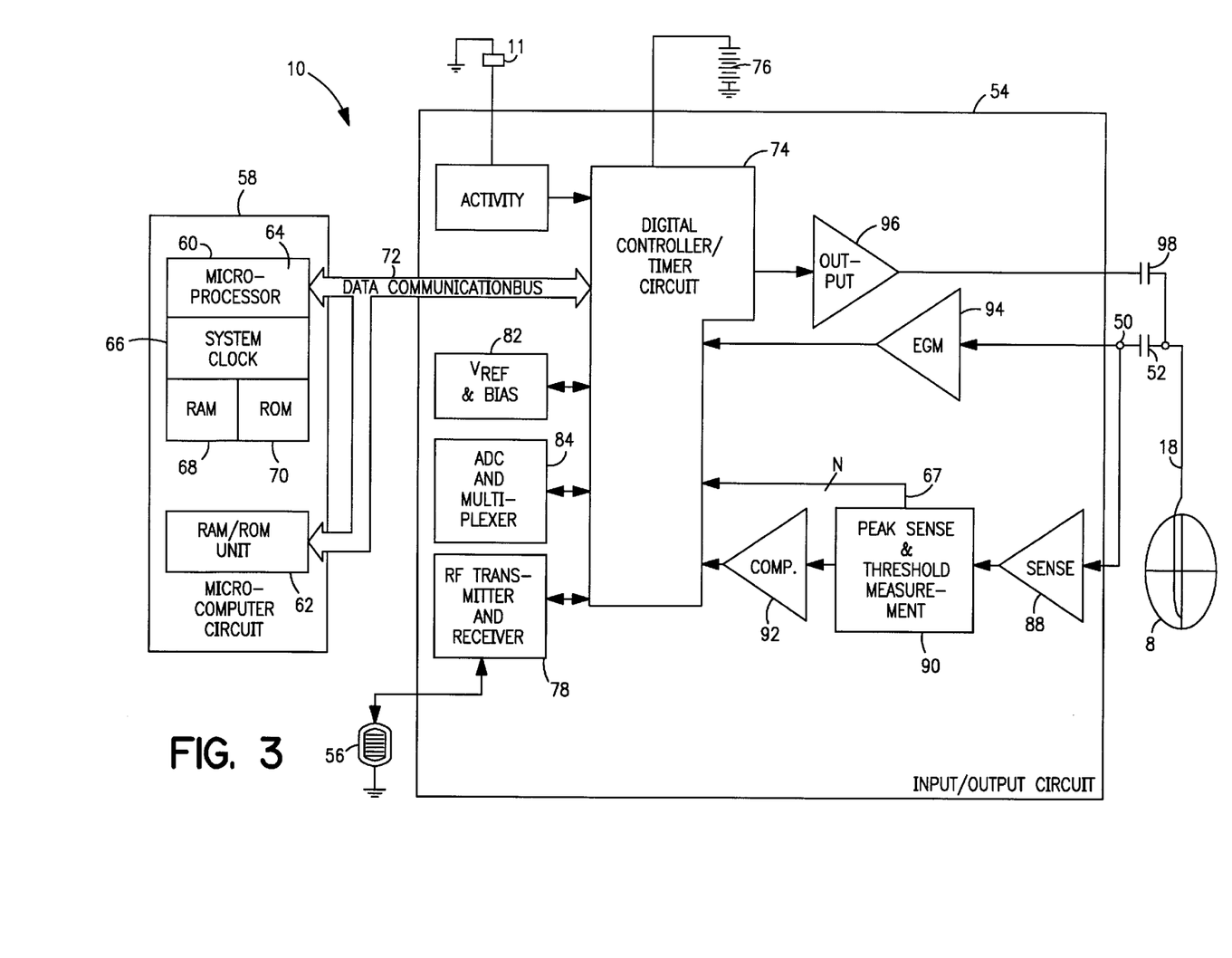
FIG. 3 is a functional block diagram of an IMD in accordance with one embodiment of the present invention where the IMD is a pacemaker.

FIG. 3 is a block diagram illustrating the constituent components of IMD 10 in accordance with one embodiment of the present invention, where IMD 10 is pacemaker having a microprocessor-based architecture. IMD 10 is shown as including activity sensor or accelerometer 11, which is preferably a piezoceramic accelerometer bonded to a hybrid circuit located inside enclosure 14. Activity sensor 11 typically (although not necessarily) provides a sensor output that varies as a function of a measured parameter relating to a patients metabolic requirements. For the sake of convenience, IMD 10 in FIG. 3 is shown with lead 18 only connected thereto; similar circuitry and connections not explicitly shown in FIG. 3 apply to lead 16.

IMD 10 in FIG. 3 is preferably programmable by means of a programming apparatus according to the present invention and described further below. The programming apparatus may include a programmer such as the commercially available Medtronic Model 9790 programmer, which is microprocessor-based and provides a series of encoded signals to IMD 10, typically through a programming wand or head (such as that described herein) which transmits or telemeters radio-frequency (RF) encoded signals to IMD 10. Such a telemetry system is described in U.S. Pat. No. 5,354,319 to Wyborny et al. The programming methodology disclosed in Wyborny et al.'s '319 patent is identified herein for illustrative purposes only. Any of a number of suitable programming and telemetry methodologies known in the art may be employed so long as the desired information is transmitted to and from IMD 10.

As shown in FIG. 3, lead 18 is coupled to node 50 in IMD 10 through input capacitor 52. Activity sensor or accelerometer 11 is most preferably attached to a hybrid circuit located inside hermetically sealed enclosure 14 of IMD 10. The output signal provided by activity sensor 11 is coupled to input/output circuit 54. Input/output circuit 54 contains analog circuits for interfacing to heart 8, activity sensor 11, antenna 56 and circuits for the application of stimulating pulses to heart 8. The rate of heart 8 is controlled by software-implemented algorithms stored in microcomputer circuit 58.

Microcomputer circuit 58 preferably comprises on-board circuit 60 and off-board circuit 62. Circuit 58 may correspond to a microcomputer circuit disclosed in U.S. Pat. No. 5,312,453 to Shelton et al. On-board circuit 60 preferably includes microprocessor 64, system clock circuit 66 and on-board RAM 68 and ROM 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 are powered by an appropriate implantable battery power source 76 in accordance with common practice in the art. For the sake of clarity, the coupling of battery power to the various components of IMD 10 is not shown in the Figures. Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,556,063 issued to Thompson et al., or to that disclosed in the above-referenced '319 patent to Wyborny et al. It is generally preferred that the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

$V_{REF}$ and Bias circuit 82 (see FIG. 3) most preferably generates stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of IMD 10 are coupled by data bus 72 to digital controller/timer circuit 74, where digital timers and counters establish the overall escape interval of the IMD 10 as well as various refractory, blanking and other timing windows for controlling the operation of peripheral components disposed within input/output circuit 54.

Digital controller/timer circuit 74 is preferably coupled to sensing circuitry, including sense amplifier 88, peak sense and threshold measurement unit 90 and comparator/threshold detector 92. Circuit 74 is further preferably coupled to electrogram (EGM) amplifier 94 for receiving amplified and processed signals sensed by lead 18. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is then provided to comparator/threshold detector 92. By way of example, sense amplifier 88 may correspond to that disclosed in U.S. Pat. No. 4,379,459 to Stein.

The electrogram signal provided by EGM amplifier 94 is employed when IMD 10 is being interrogated by an external programmer to transmit a representation of a cardiac analog electrogram, See, for example, U.S. Pat. No. 4,556,063 to Thompson et al. Output pulse generator 96 provides pacing stimuli to patient's heart 8 through coupling capacitor 98, for example, in response to a pacing trigger signal provided by digital controller/timer circuit 74 each time the escape interval times out, in response to an externally transmitted pacing command or in response to other stored commands as is well known in the pacing art. By way of example, output amplifier 96 may correspond generally to an output amplifier disclosed in U.S. Pat. No. 4,476,868 to Thompson.

The specific embodiments of input amplifier 88, output amplifier 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 8.

In some preferred embodiments of the present invention, IMD 10 may operate in various non-rate-responsive modes, including, but not limited to, DDD, DDI, VVI, VOO and VVT modes. In other preferred embodiments of the present invention, IMD 10 may operate in various rate-responsive modes, including, but not limited to, DDDR, DDIR, VVIR, VOOR and VVTR modes. Some embodiments of the present invention are capable of operating in both non-rate-responsive and rate-responsive modes. Moreover, in various embodiments of the present invention, IMD 10 may be programmably configured to operate so that it varies the rate at which it delivers stimulating pulses to heart 8 only in response to one or more selected sensor outputs being generated. Numerous pacemaker features and functions not explicitly mentioned herein may be incorporated into IMD 10 while remaining within the scope of the present invention.

The present invention is not limited in scope to single-sensor or dual-sensor pacemakers, and is not limited to IMD's comprising activity or pressure sensors only. Further, the present invention is not limited in scope to single-chamber pacemakers, single-chamber leads for pacemakers or single-sensor or dual-sensor leads for pacemakers. Thus, various embodiments of the present invention may be practiced in conjunction with more than two leads or with multiple-chamber pacemakers, for example. At least some embodiments of the present invention may be applied equally well in the contexts of single-, dual-, triple- or quadruple-chamber pacemakers or other types of IMD's. See, for example, U.S. Pat. No. 5,800,465 to Thompson et al.

IMD 10 may also be a pacemaker-cardioverter-defibrillator ("PCD") corresponding to any of numerous commercially available implantable PCD's. Various embodiments of the present invention may be practiced in conjunction with PCD's such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless and U.S. Pat. No. 4,821,723 to Baker, Jr. et al.

Figure 4:
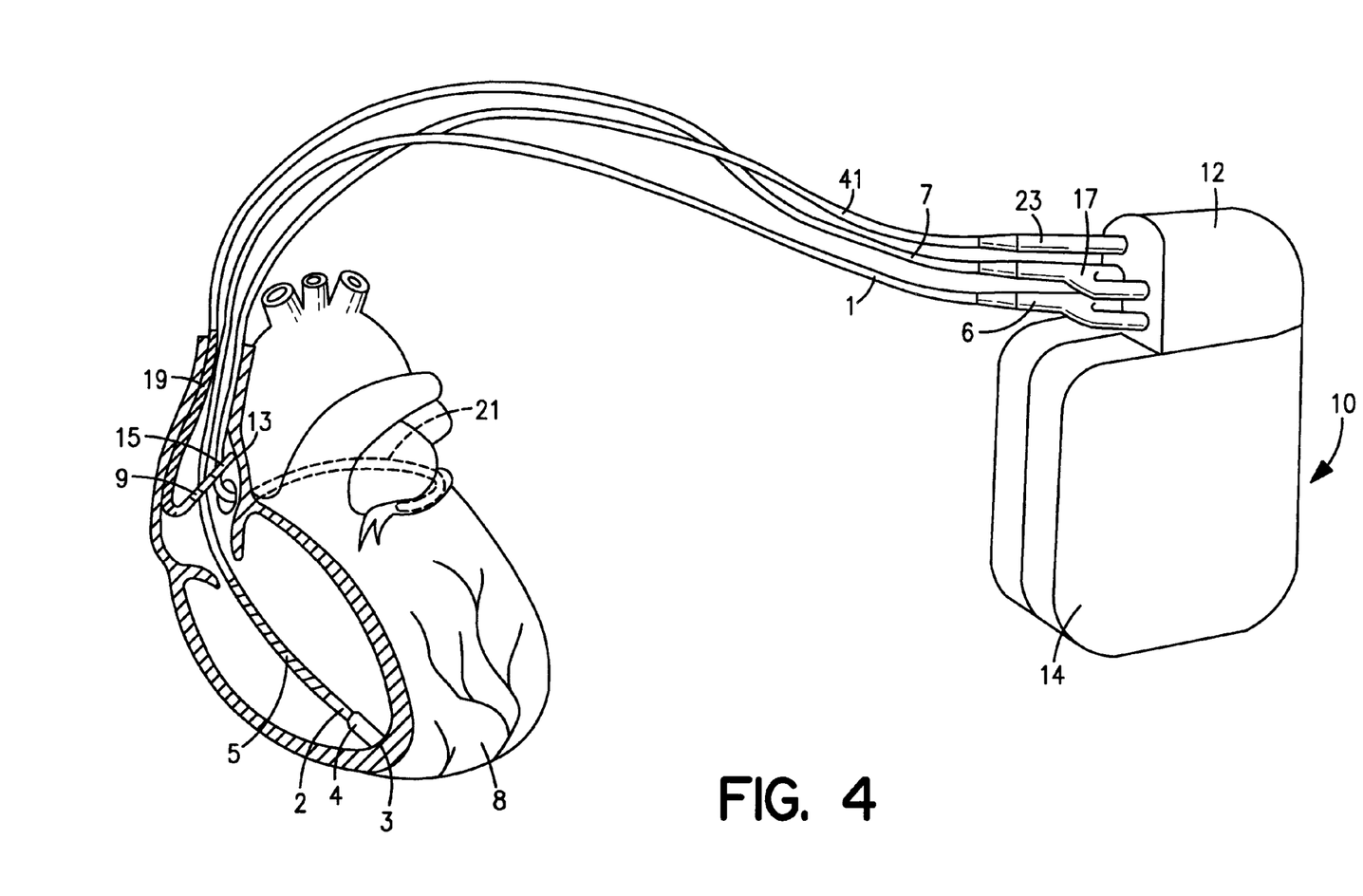
FIG. 4 is an IMD in accordance with another embodiment of the invention, wherein the IMD is an implantable pacemaker-cardioverter-defibrillator (PCD)
Figure 5:
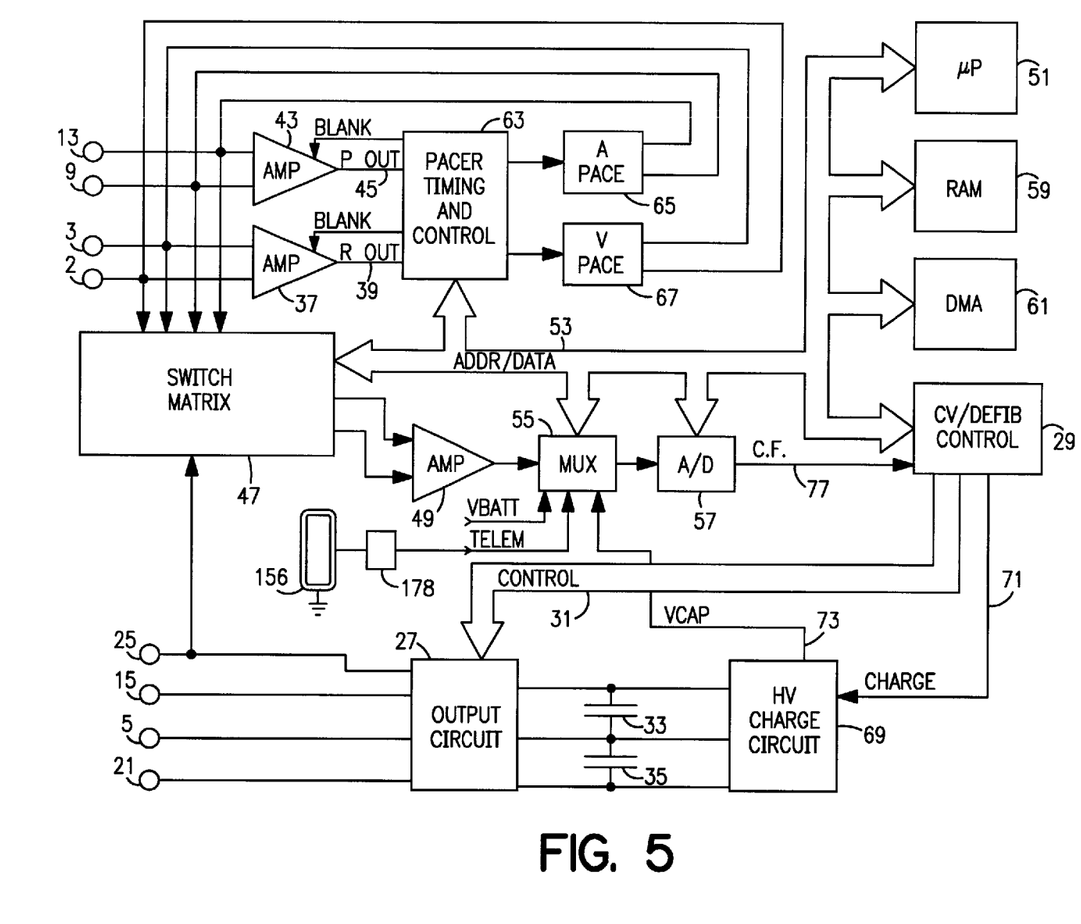
FIG. 5 is a functional block diagram of the IMD of FIG. 4.

FIGS. 4 and 5 illustrate one embodiment of IMD 10 and a corresponding lead set of the present invention, where IMD 10 is a PCD. In FIG. 4, the ventricular lead takes the form of leads disclosed in U.S. Pat. Nos. 5,099,838 and 5,314,430 to Bardy, and includes an elongated insulative lead body 1 carrying three concentric coiled conductors separated from one another by tubular insulative sheaths. Located adjacent the distal end of lead 1 are ring electrode 2, extendable helix electrode 3 mounted retractably within insulative electrode head 4 and elongated coil electrode 5. Each of the electrodes is coupled to one of the coiled conductors within lead body 1. Electrodes 2 and 3 are employed for cardiac pacing and for sensing ventricular depolarizations. At the proximal end of the lead is bifurcated connector 6 which carries three electrical connectors, each coupled to one of the coiled conductors. Defibrillation electrode 5 may be fabricated from platinum, platinum alloy or other materials known to be usable in implantable defibrillation electrodes and may be about 5 cm in length.

The atrial/SVC lead shown in FIG. 4 includes elongated insulative lead body 7 carrying three concentric coiled conductors separated from one another by tubular insulative sheaths corresponding to the structure of the ventricular lead. Located adjacent the J-shaped distal end of the lead are ring electrode 9 and extendable helix electrode 13 mounted retractably within an insulative electrode head 15. Each of the electrodes is coupled to one of the coiled conductors within lead body 7. Electrodes 13 and 9 are employed for atrial pacing and for sensing atrial depolarizations. Elongated coil electrode 19 is provided proximal to electrode 9 and coupled to the third conductor within lead body 7. Electrode 19 preferably is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is bifurcated connector 17 carrying three electrical connectors, each coupled to one of the coiled conductors.

The coronary sinus lead shown in FIG. 4 assumes the form of a coronary sinus lead disclosed in the above cited '838 patent issued to Bardy, and includes elongated insulative lead body 41 carrying one coiled conductor coupled to an elongated coiled defibrillation electrode 21. Electrode 21, illustrated in broken outline in FIG. 4, is located within the coronary sinus and great vein of the heart. At the proximal end of the lead is connector plug 23 carrying an electrical connector coupled to the coiled conductor. The coronary sinus/great vein electrode 41 may be about 5 cm in length.

The implantable PCD is shown in FIG. 4 in combination with leads 1, 7 and 41, and lead connector assemblies 23, 17 and 6 inserted into connector block 12. Optionally, insulation of the outward facing portion of housing 14 of PCD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 14 serves as a subcutaneous defibrillation electrode to defibrillate either the atria or ventricles. Lead configurations other than those shown in FIG. 4 may be practiced in conjunction with the present invention, such as those shown in U.S. Pat. No. 5,690,686 to Min et al.

FIG. 5 is a functional schematic diagram of one embodiment of an implantable PCD of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies.

The PCD is provided with an electrode system. If the electrode configuration of FIG. 4 is employed, the electrode configuration correspondence may be as follows. Electrode 25 in FIG. 5 includes the uninsulated portion of the housing of the PCD. Electrodes 25, 15, 21 and 5 are coupled to high voltage output circuit 27, which includes high voltage switches controlled by CV/defib control logic 29 via control bus 31. Switches disposed within circuit 27 determine which electrodes are employed and which electrodes are coupled to the positive and negative terminals of the capacitor bank (which includes capacitors 33 and 35) during delivery of defibrillation pulses.

Electrodes 2 and 3 are located on or in the ventricle and are coupled to the R-wave amplifier 37, which preferably takes the form of an automatic gain controlled amplifier providing an adjustable sensing threshold as a function of the measured R-wave amplitude. A signal is generated on R-out line 39 whenever the signal sensed between electrodes 2 and 3 exceeds the present sensing threshold.

Electrodes 9 and 13 are located on or in the atrium and are coupled to the P-wave amplifier 43, which preferably also takes the form of an automatic gain controlled amplifier providing an adjustable sensing threshold as a function of the measured P-wave amplitude. A signal is generated on P-out line 45 whenever the signal sensed between electrodes 9 and 13 exceeds the present sensing threshold. The general operation of R-wave and P-wave amplifiers 37 and 43 may correspond to that disclosed in U.S. Pat. No. 5,117,824, to Keimel et al.

Switch matrix 47 is used to select which of the available electrodes are coupled to wide band (0.5–200 Hz) amplifier 49 for use in digital signal analysis. Selection of electrodes is controlled by the microprocessor 51 via data/address bus 53, which selection may be varied as desired. Signals from the electrodes selected for coupling to bandpass amplifier 49 are provided to multiplexer 55, and thereafter converted to multi-bit digital signals by N/D converter 57, for storage in random access memory 59 under control of direct memory access circuit 61. Microprocessor 51 may employ digital signal analysis techniques to characterize the digitized signals stored in random access memory 59 to recognize and classify the patient's heart rhythm employing any of the numerous signal processing methodologies known in the art.

The remainder of the circuitry is dedicated to the provision of cardiac pacing, cardioversion and defibrillation therapies, and, for purposes of the present invention may correspond to circuitry known to those skilled in the art. The following exemplary apparatus is disclosed for accomplishing pacing, cardioversion and defibrillation functions. Pacer timing/control circuitry 63 preferably includes programmable digital counters which control the basic time intervals associated with DDD, VVI, DVI, VDD, AAI, DDI and other modes of single and dual chamber pacing well known to the art. Circuitry 63 also preferably controls escape intervals associated with anti-tachyarrhythmia pacing in both the atrium and the ventricle, employing any anti-tachyarrhythmia pacing therapies known in the art.

Intervals defined by pacing circuitry 63 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 51, in response to stored data in memory 59 and are communicated to pacing circuitry 63 via address/data bus 53. Pacer circuitry 63 also determines the amplitude of the cardiac pacing pulses under control of microprocessor 51.

During pacing, escape interval counters within pacer timing/control circuitry 63 are reset upon sensing of R-waves and P-waves as indicated by signals on lines 39 and 45, and in accordance with the selected mode of pacing on time-out trigger generation of pacing pulses by pacer output circuitry 65 and 67, which are coupled to electrodes 9, 13, 2 and 3. Escape interval counters are also reset on generation of pacing pulses and thereby control the basic timing of cardiac pacing functions, including anti-tachyarrhythmia pacing. The durations of the intervals defined by escape interval timers are determined by microprocessor 51 via data/address bus 53. The value of the count present in the escape interval counters when reset by sensed R-waves and P-waves may be used to measure the durations of R-R intervals, P-P intervals, P-R intervals and R-P intervals, which measurements are stored in memory 59 and used to detect the presence of tachyarrhythmias.

Microprocessor 51 most preferably operates as an interrupt driven device, and is responsive to interrupts from pacer timing/control circuitry 63 corresponding to the occurrence of sensed P-waves and R-waves and corresponding to the generation of cardiac pacing pulses. Those interrupts are provided via data/address bus 53. Any necessary mathematical calculations to be performed by microprocessor 51 and any updating of the values or intervals controlled by pacer timing/control circuitry 63 take place following such interrupts.

Detection of atrial or ventricular tachyarrhythmias, as employed in the present invention, may correspond to tachyarrhythmia detection algorithms known in the art. For example, the presence of an atrial or ventricular tachyarrhythmia may be confirmed by detecting a sustained series of short R-R or P-P intervals of an average rate indicative of tachyarrhythmia or an unbroken series of short R-R or P-P intervals. The suddenness of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann et al., U.S. Pat. No. 4,880,005 issued to Pless et al. and U.S. Pat. No. 4,830,006 issued to Haluska et al. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, IEEE Computer Society Press, pages 167–170. Atrial fibrillation detection methodologies are disclosed in Published PCT Application Ser. No. US92/02829, Publication No. WO92/18198, by Adams et al., and in the article "Automatic Tachycardia Recognition", by Arzbaecher et al., published in PACE, May–June, 1984, pp. 541–547.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 51 into the pacer timing and control circuitry 63, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al., U.S. Pat. No. 4,880,005, issued to Pless et al., U.S. Pat. No. 4,726,380, issued to Vollmann et al. and U.S. Pat. No. 4,587,970, issued to Holley et al., may also be employed.

In the event that generation of a cardioversion or defibrillation pulse is required, microprocessor 51 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 51 activates cardioversion/defibrillation control circuitry 29, which initiates charging of the high voltage capacitors 33 and 35 via charging circuit 69, under the control of high voltage charging control line 71. The voltage on the high voltage capacitors is monitored via VCAP line 73, which is passed through multiplexer 55 and, in response to reaching a predetermined value set by microprocessor 51, results in generation of a logic signal on Cap Full (CF) line 77 to terminate charging. Thereafter, timing of the delivery of the defibrillation or cardioversion pulse is controlled by pacer timing/control circuitry 63. Following delivery of the fibrillation or tachycardia therapy microprocessor 51 returns the device to q cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al. and U.S. Pat. No. 4,316,472 to Mirowski et al. However, any known cardioversion or defibrillation pulse control circuitry is believed to be usable in conjunction with various embodiments of the present invention. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., may also be employed.

Continuing to refer to FIG. 5, delivery of cardioversion or defibrillation pulses is accomplished by output circuit 27 under the control of control circuitry 29 via control bus 31. Output circuit 27 determines whether a monophasic or biphasic pulse is delivered, the polarity of the electrodes and which electrodes are involved in delivery of the pulse. Output circuit 27 also includes high voltage switches which control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. Examples of output circuitry for delivery of biphasic pulse regimens to multiple electrode systems may be found in U.S. Pat. No. 4,953,551 to Mehra et al. and in U.S. Pat. No. 4,727,877 to Kallock.

Like the pacemaker IMD illustrated in FIG. 3, the PCD of FIG. 5 also includes RF transmitter and receiver telemetry unit 178 coupled to antenna 156 to permit communication with the programmer as described herein.

An example of circuitry which may be used to control delivery of monophasic pulses is disclosed in U.S. Pat. No. 5,163,427 to Keimel. Output control circuitry similar to that disclosed in the above cited patent issued to Mehra et al. or U.S. Pat. No. 4,800,883 to Winstrom, may also be used in conjunction with various embodiments of the present invention to deliver biphasic pulses.

Alternatively, IMD 10 may be an implantable nerve stimulator or muscle stimulator such as that disclosed in U.S. Pat. No. 5,199,428 to Obel et al., U.S. Pat. No. 5,207,218 to Carpentier et al. or U.S. Pat. No. 5,330,507 to Schwartz, or an implantable monitoring device such as that disclosed in U.S. Pat. No. 5,331,966 issued to Bennett et al. The present invention is believed to find wide application to any form of implantable electrical device.

Various embodiments of IMD 10 are described above. Attention is now directed to programming wands, programming systems, and methods for programming IMDs, such as those described above, in accordance with the present invention.

Figure 6:
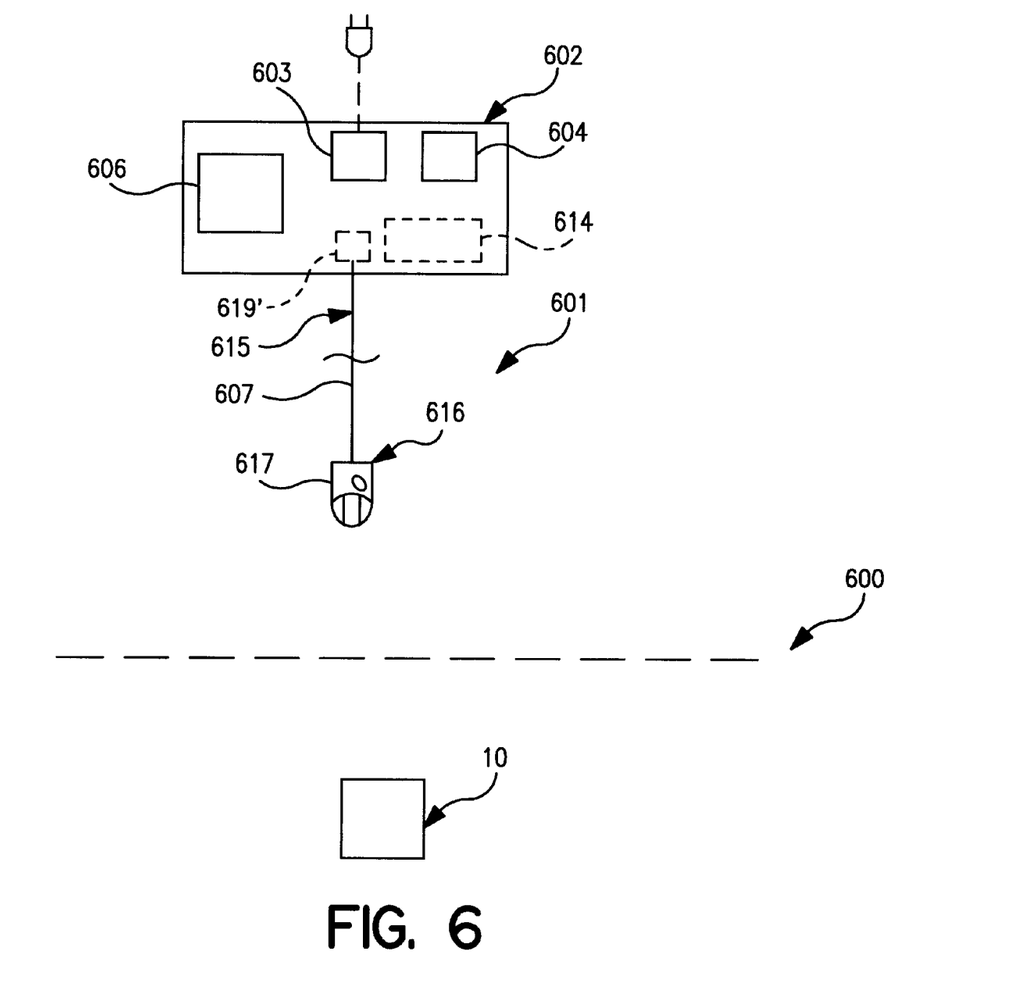
FIG. 6 is a functional block diagram of a programming system in accordance with one embodiment of the invention.

FIG. 6 diagrammatically illustrates a programming system 600 for programming IMD 10 in accordance with one embodiment of the invention. System 600 may include a programmer or programming apparatus 601 and IMD 10. Programmer 601 preferably includes a programming device 602 adapted for table- or cart-top use. Device 602 may include programming circuitry 604 which executes programming software to control programmer 601 during operation. Device 602 may also include a power supply, e.g., rechargeable battery source 603 and/or externally-powered AC, to power programmer 601. In one embodiment, programming device 602 is similar to the model 9790 programmer sold by Medtronic, Inc. For the sake of clarity, the electrical coupling of the various components is not fully illustrated in FIG. 6.

To monitor programming system 600, an output device, e.g., a video display 606, may also be incorporated into device 602 as shown in FIG. 6. Other output devices, e.g., printers, disk drives, may also be provided. In one embodiment, programming circuitry 604 of programmer 601 interfaces with the operator via graphical user interface (GUI) programming software such as the icon-based "Vision" software produced by Medtronic, Inc. Such GUIs may preferably be IMD-specific to present at least programming information to the user, e.g., via display 606. Nonetheless, a non-specific GUI, e.g., Microsoft "Windows," may also be used. Programming information, as used herein, generally refers to any information relating to or otherwise beneficial to the programming process, e.g., programming parameters and instructions, device (IMD) status information, patient status information (erg., ECG), etc. The operator communicates with the programming circuitry 604 via selection of menus presented by the programming software and displayed on display 606.

An auxiliary data input device 614 may optionally be provided. While shown as an integral component, input device 614 may, in another embodiment, be detached from device 602. Preferably, data input device 614 is a keyboard, similar in most respects to a conventional computer keyboard, which allows manipulation of programming software and programming circuitry 604 via keystrokes. Alternatively, device 614 may be any one of a number of other input devices, e.g., digitizing pen, which, in conjunction with visual cues provided on display 606, allows manipulation of programming circuitry 604.

Programmer 601 may further include a telemetry apparatus 615 permitting unidirectional or, more preferably, bi-directional communication with RF transmitter and receiver telemetry unit 78 (see FIG. 3) or 178. (see FIG. 5) of IMD 10. In accordance with the present invention, telemetry apparatus 615 includes a programming wand 616 tethered to device 602 by cable 607. Alternatively, wand 616 may communicate with programming circuitry 604 and other components of device 602 via wireless protocols, e.g., RF or infrared. Device 602 may optionally include a holder (not shown) for receiving wand 616 when the latter is not in use.

Figure 7:
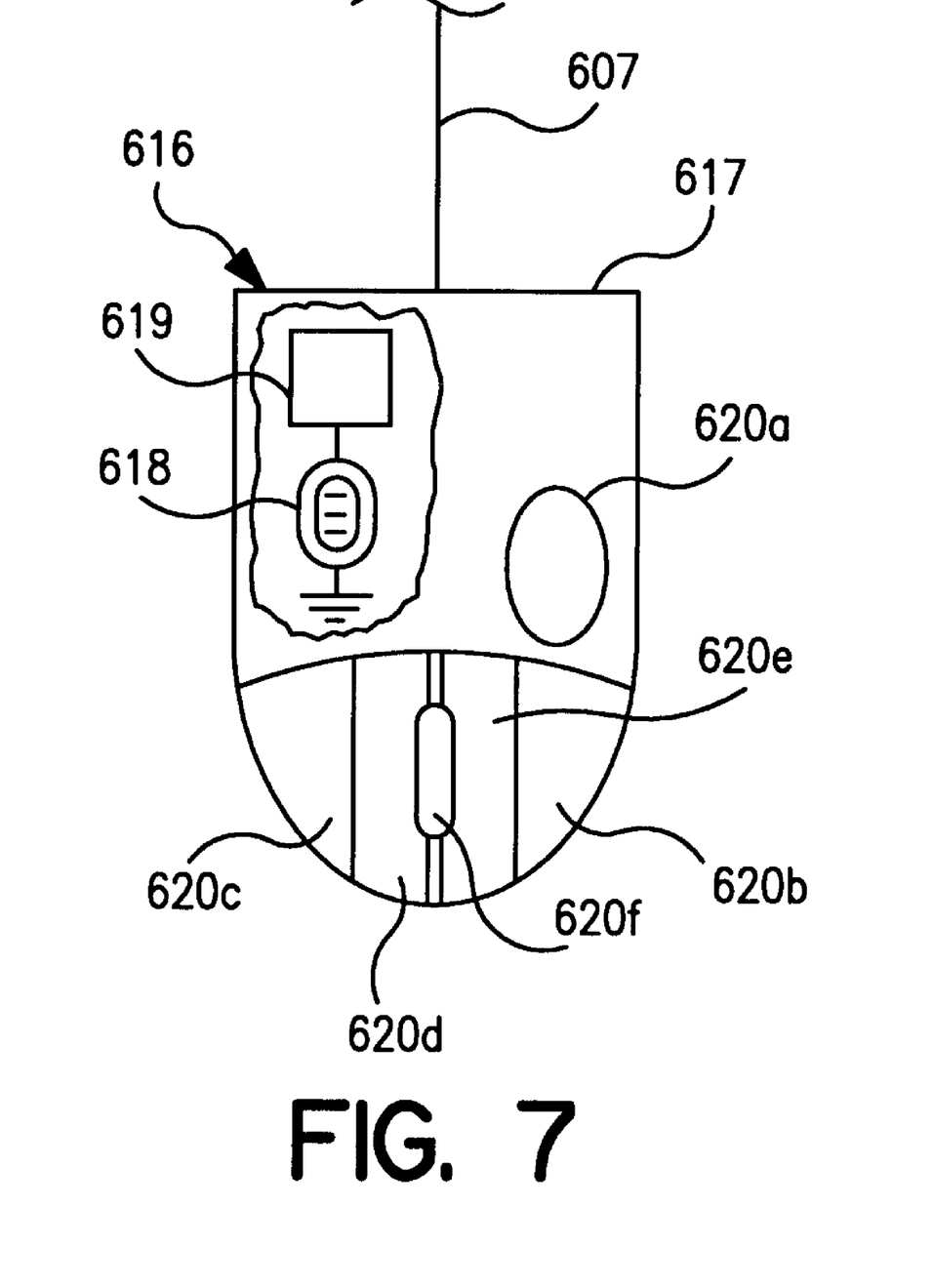
FIG. 7 is a diagrammatic view of a programming wand in accordance with one embodiment of the invention.

FIG. 7 is an enlarged diagrammatic view of a handheld programming wand 616 in accordance with one embodiment of the invention. As illustrated in this view, wand 616 includes a housing 617 enclosing antenna 618 which is coupled to transmitter circuitry. More preferably, antenna 618 is coupled to both transmitter circuitry and receiver circuitry (hereinafter referred to collectively as transceiver circuitry 619). In alternative embodiments, transceiver circuitry 619 may be located in device 602 as indicated in FIG. 6 by reference numeral 619'. Using standard communication protocols, e.g., RF, wand 616 may bi-directionally communicate via antenna 618 with IMD 10. That is, transceiver 619 may communicate via antenna 618 with antenna 56 of transmitter and receiver circuitry 78 (see FIG. 3) or antenna 156 of transmitter and receiver circuitry 178 (see FIG. 5) of IMD 10. An example of such a telemetry system is described in U.S. Pat. No. 5,354,319 to Wyborny et al. The programming methodology disclosed in to Wyborny et al.'s '319 patent is identified herein for illustrative purposes only. Any of a number of suitable programming and telemetry methodologies known in the art may be employed so long as the desired information is transmitted to and from IMD 10.

Preferred embodiments of wand 616 further include one or more input devices 620, e.g., pointing/selection devices, which are typically located on housing 617. The actual input device(s) 620 may take a variety of forms. For example, in a preferred embodiment, programming wand 616 includes at least a trackball 620a positioned for comfortable rotation/manipulation with the thumb or other finger. One or more buttons 620b–620e and a rotating scrolling wheel 620f may optionally be included (for convenience, all input devices are generically denoted hereinafter by reference numeral 620).

Input devices 620 permit operator interaction with and control of the programming software when wand 616 is held in proximity to the patient. For example, by rolling trackball 620a, the operator may move the cursor on display 606 to the desired location. Buttons 620b and 620c may function similar to the left and right mouse buttons of a conventional computer mouse, permitting software option selection based on cursor location. Buttons 620d and 620e may have functions specific to IMD programming, e.g., depressing button 620d may execute an "interrogate" command while pressing button 620e may execute a "program" command. Scrolling wheel 620f may permit scrolling through display pages or lists of tabular information, e.g., scrolling through tables of IMD parameter values. Scrolling wheel 620f may also be depressed to select a highlighted value.

While the invention is described herein with respect to specific input devices, e.g., trackball 620a, buttons 620b–620e, and scrolling wheel 620f, other embodiments may utilize most any other type of input device (e.g., touch pad, joystick) or combination of input devices without departing from the scope of the invention.

In use, programming wand 616 is preferably held over the patient in the general vicinity of IMD 10. Wand 616 may have a shape that is similar in many respects to a common trackball computer input device, e.g., those produced by Microsoft Corp. and Logitech. However, because programming wand 616 is typically supported by the operator's hand during use, a shape that is particularly conducive to manipulation of the input devices 620 while at the same time being supported in the hand is preferred. As a result, programming wands of the present invention may include features that assist the operator in supporting the wand. For instance, one or more straps or similar devices (not shown) may secure wand 616 to the operator's hand. Alternatively, wand 616 may have other shapes, e.g., a pistol grip, that provide convenient gripping while still permitting the operator to comfortably manipulate the input devices 620.

While described herein with application to cart-top cardiac programmers, programming wands and methods of the present invention may function with most any programming system. For instance, wands of the present invention may be combined with body-worn programmers such as those taught in Assignee's copending U.S. patent application Ser. No. 09/727,463 (Attorney Docket No. P-8942, B. Ferek-Petric), filed Dec. 4, 2000 and entitled "Implantable Medical Device Programmers Having Headset Video And Methods Of Using Same," now U.S. Pat. No. 6,442,430. When so combined, the operator may view the display and interface without turning away from the direction of the patient.

Similarly, programming wands and methods in accordance with the present invention may be used in conjunction with other IMDs, e.g., neurologic implants, nerve stimulators, muscle stimulators, or, alternatively, external medical devices, erg., respiratory monitors, that may incorporate the circuits necessary for communication and operation as described herein. In addition, programmers in accordance with the present invention may be adapted to function not only with IMDs, but also with other medical devices and systems now known and those not yet commercially available.

By incorporating one or more input devices into the programming wand, the operator is able to conduct the programming process essentially with one hand, i.e., the operator is not required to hold the wand with one hand while manipulating a pen, keyboard or other input device with the other.

The complete disclosure of the patents, patent documents (including patent applications), and publications cited in the Background, Detailed Description and elsewhere herein are incorporated by reference in their entirety as if each were individually incorporated.

The preceding specific embodiments are illustrative of the practice of the invention. It is to be understood, therefore, that other expedients known to those skilled in the art or disclosed herein may be employed without departing from the invention or the scope of the appended claims. For example, the present invention is not limited to the use of IMDs for cardiac therapy but may, as mentioned above, be used with most any medical device, implanted or external. The present invention further includes within its scope methods of making and using the programmers and systems described herein above.

What is claimed is:

1. A method for communicating with an implantable medical device, the method comprising:
    providing an implantable medical device within a body, the implantable medical device having at least receiver circuitry;
    providing a programming apparatus, comprising;
        a programming device having programming circuitry operable for use in programming the implantable medical device;
        a programming wand for communicating with the implantable medical device, the programming wand comprising:
            a housing;
            transmitter circuitry within the housing, the transmitter circuitry compatible with the receiver circuitry of the implantable medical device;
            an antenna associated with the housing, the antenna coupled to the transmitter circuitry, wherein the antenna is operable for transmitting programming information to the receiver circuitry of the implantable medical device; and
            an input device coupled to the housing, the input device operable for use in permitting operator control of the programming device;
    positioning the programming wand proximate to the implantable medical device;
    holding the programming wand with an operator's first hand;
    transmitting programming instructions from the programming device to the implantable medical device via the programming wand;
    manipulating one or more input devices located on the programming wand to control the programming apparatus with the operator's first hand; and
    maintaining the operator's second hand free to perform tasks other than controlling the programming apparatus.

2. The method of claim 1, wherein manipulating the one or more devices comprises rotating a trackball.

3. The method of claim 1, wherein manipulating the one or more input devices comprises rotating a scrolling wheel.

4. The method of claim 1, wherein manipulating the one or more input devices comprises depressing a button.

5. The method of claim 1, further comprising transmitting status information from the implantable medical device to the programming wand.

6. The method of claim 1, wherein the medical device is a cardiac pacing device.

7. The method of claim 1, wherein the cardiac pacing device is at least one of a pacemaker, cardioverter, defibrillator.

* * * * *